(12) United States Patent
Talebi Sarvari

(10) Patent No.: US 9,978,559 B2
(45) Date of Patent: May 22, 2018

(54) METHOD AND DEVICE FOR TIME-RESOLVED PUMP-PROBE ELECTRON MICROSCOPY

(71) Applicant: Max-Planck-Gesellschaft zur Foerderung der Wissenschaften e.V., Munich (DE)

(72) Inventor: Nahid Talebi Sarvari, Stuttgart (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days. days.

(21) Appl. No.: 15/505,649

(22) PCT Filed: Jul. 22, 2015

(86) PCT No.: PCT/EP2015/001509
§ 371 (c)(1),
(2) Date: Feb. 22, 2017

(87) PCT Pub. No.: WO2016/029984
PCT Pub. Date: Mar. 3, 2016

(65) Prior Publication Data
US 2017/0271123 A1    Sep. 21, 2017

(30) Foreign Application Priority Data
Aug. 25, 2014 (EP) .................................. 14002946

(51) Int. Cl.
*G01N 23/00* (2006.01)
*H01J 37/22* (2006.01)
(Continued)

(52) U.S. Cl.
CPC .......... *H01J 37/228* (2013.01); *H01J 37/226* (2013.01); *H01J 37/244* (2013.01); *H01J 37/26* (2013.01);
(Continued)

(58) Field of Classification Search
None
See application file for complete search history.

(56) References Cited

U.S. PATENT DOCUMENTS 3,085,406 A * 4/1963 Hanebuth ................. F16C 1/06
138/131
8,085,406 B2  12/2011 Petek et al.
(Continued)

FOREIGN PATENT DOCUMENTS

EP    2784798 A1 * 10/2014  ......... G01N 23/2251
EP    2784798 B1 *  3/2016  ......... G01N 23/2251
(Continued)

OTHER PUBLICATIONS

Adamo et al. (2009). The light well: a tunable free-electron light source on a chip. Physical review letters, 103(11), 113901: 1-4.
(Continued)

*Primary Examiner* — Andrew Smyth
(74) *Attorney, Agent, or Firm* — Caesar Rivise, PC

(57) ABSTRACT

A method of time-resolved pump-probe electron microscopy, comprises the steps of irradiating a sample (1) with a photonic pump pulse (2) being directed on a pump pulse path (3) from a photonic source to the sample (1), irradiating the sample (1) with an electron probe pulse (4) being directed on an electron pulse path (5) from an electron pulse source (10) to the sample (1), wherein the photonic pump pulse (2) and the electron probe pulse (4) arrive at the sample (1) with a predetermined temporal relationship relative to each other, and detecting a sample response to the electron probe pulse (4) irradiation with a detector device (20), wherein the photonic source comprises a photonic lattice structure (30) being arranged adjacent to the electron pulse path (5), and the photonic pump pulse (2) is created by an interaction of the electron probe pulse (4) with the photonic lattice structure (30). Furthermore, an electron
(Continued)

microscopy apparatus, configured for time-resolved pump-probe electron microscopy, and a sample supply device (200) for an electron microscopy apparatus (100) are described.

18 Claims, 6 Drawing Sheets

(51) Int. Cl.
*H01J 37/244* (2006.01)
*H01J 37/26* (2006.01)

(52) U.S. Cl.
CPC ............ *H01J 2237/2445* (2013.01); *H01J 2237/24475* (2013.01); *H01J 2237/24585* (2013.01); *H01J 2237/2626* (2013.01)

(56) References Cited

U.S. PATENT DOCUMENTS

| | | | | |
|---|---|---|---|---|
| 2012/0293791 A1* | 11/2012 | Milas | ............... | H01J 37/20 356/72 |
| 2013/0234023 A1* | 9/2013 | Zewail | ............... | H01J 37/22 250/307 |
| 2014/0158883 A1* | 6/2014 | Zewail | ............... | H01J 37/22 250/305 |
| 2014/0297205 A1* | 10/2014 | Sarvari | ............ | G01N 23/2251 702/57 |

FOREIGN PATENT DOCUMENTS

| | | | | |
|---|---|---|---|---|
| WO | 2005098895 A2 | 10/2005 | | |
| WO | WO 2005098895 A2 * | 10/2005 | ............ | H01J 37/065 |
| WO | WO 2005098895 A9 * | 3/2006 | ............ | H01J 37/065 |
| WO | WO 2005098895 A3 * | 12/2006 | ............ | H01J 37/065 |

OTHER PUBLICATIONS

Adamo et al. (2010). Tuneable electron-beam-driven nanoscale light source. Journal of optics, 12(2), 024012: 1-5.
Adamo et al. (2012). Electron-beam-driven collective-mode metamaterial light source. Physical review letters, 109(21), 217401: 1-5.
Aidelsburger et al. (2010). Single-electron pulses for ultrafast diffraction. Proceedings of the National Academy of Sciences, 107(46), 19714-19719.
Baum, P. (2013). On the physics of ultrashort single-electron pulses for time-resolved microscopy and diffraction. Chemical Physics, 423, 55-61.
Dohler et al. (1987). Recent orotron results. In Electron Devices Meeting, 1987 International (pp. 303-306). IEEE.
Doucas et al. (1992). First observation of Smith-Purcell radiation from relativistic electrons. Physical review letters, 69(12), 632-634.
Gahlmann et al. (2008). Ultrashort electron pulses for diffraction, crystallography and microscopy: theoretical and experimental resolutions. Physical Chemistry Chemical Physics, 10(20), 2894-2909.
Gover et al. (1981). A unified theory of magnetic bremsstrahlung, electrostatic bremsstrahlung, Compton-Raman scattering, and Cerenkov-Smith-Purcell free-electron lasers. IEEE Journal of Quantum Electronics, 17(7), 1196-1215.
Gliserin et al. (2012). Compression of single-electron pulses with a microwave cavity. New Journal of Physics, 14(7), 073055: 1-17.
Kapp et al. (2004). Modification of a scanning electron microscope to produce Smith-Purcell radiation. Review of Scientific Instruments, 75(11), 4732-4741.
Kapp et al. (2006). A flexible instrument control and image acquisition system for a scanning electron microscope. Journal of microscopy, 223(2), 140-149.
Sciaini et al. (2011). Femtosecond electron diffraction: heralding the era of atomically resolved dynamics. Reports on Progress in Physics, 74(9), 096101: 1-36.
Talebi et al. (2013). Numerical simulations of interference effects in photon-assisted electron energy-loss spectroscopy. New Journal of Physics, 15(5), 053013: 1-15.
Urata et al. (1998). Superradiant smith-purcell emission. Physical review letters, 80(3), 516-519.
Walmsley et al. (2009). Characterization of ultrashort electromagnetic pulses. Advances in Optics and Photonics, 1(2), 308-437.
Yurtsever et al. (2012). Subparticle ultrafast spectrum imaging in 4D electron microscopy. Science, 335(6064), 59-64.
International Search Report from corresponding PCT/EP2015/001509 dated Oct. 23, 2015.

* cited by examiner

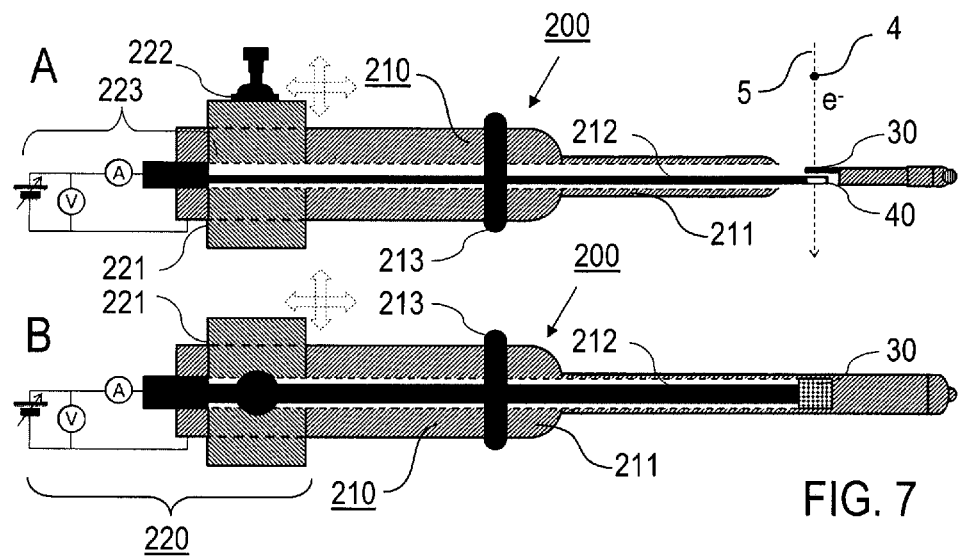
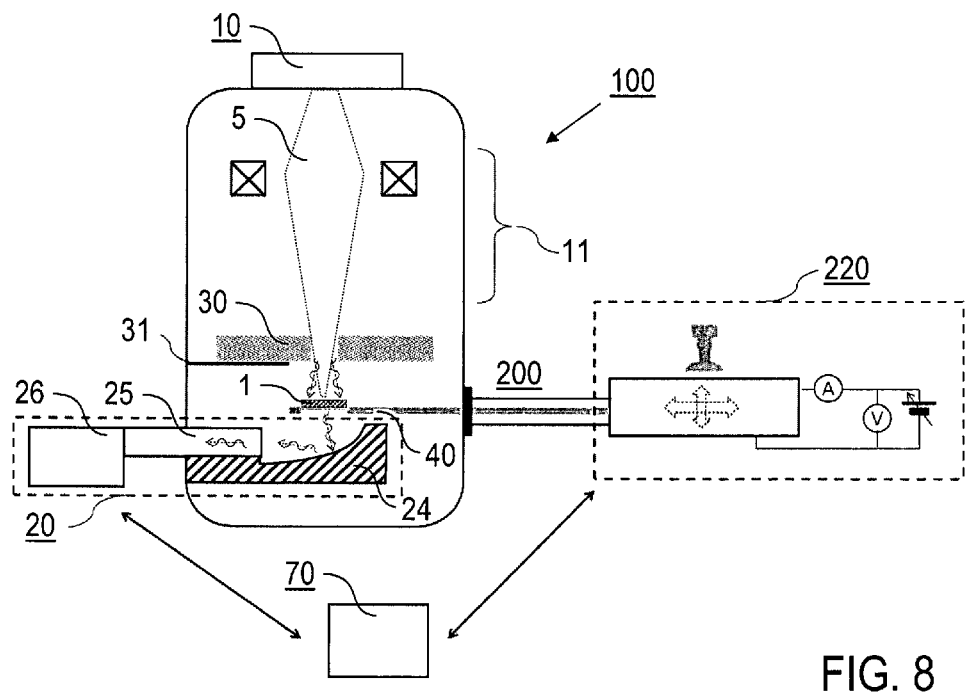

METHOD AND DEVICE FOR TIME-RESOLVED PUMP-PROBE ELECTRON MICROSCOPY

CROSS-REFERENCE TO RELATED APPLICATIONS

This application is the U.S. National Phase Application of PCT/EP2015/001509, filed Jul. 22, 2015, which claims priority from EP 14002946.3, filed Aug. 25, 2014, the contents of which applications are incorporated herein by reference in their entireties for all purposes.

FIELD OF THE INVENTION

The present invention relates to a method of time-resolved pump-probe electron microscopy, wherein a sample is subjected to a photonic pump pulse and an electron probe pulse. Furthermore, the invention relates to an electron microscopy apparatus, which is adapted for time-resolved pump-probe electron microscopy. Applications of the invention are available in electron microscopy techniques, like e. g. diffraction, imaging and/or spectroscopy methods.

BACKGROUND OF THE INVENTION

In the present specification, reference is made to the following publications illustrating conventional techniques.
[1] WO 2005/098895 A2;
[2] A. Yurtsever et al. "Subparticle Ultrafast Spectrum Imaging in 4D Electron Microscopy" in "Science" vol. 335, 2012, pp. 59-64;
[3] G. Sciaini et al. "Femtosecond electron diffraction: heralding the era of atomically resolved dynamics" in "Reports on Progress in Physics" vol. 74, 2011, pp. 096101-096137;
[4] P. Baum, "On the physics of ultrashort single-electron pulses for time-resolved microscopy and diffraction" in "Chemical Physics" vol. 423, 2013, pp. 55-61;
[5] A. Gahlmann et al. "Ultrashort electron pulses for diffraction, crystallography and microscopy: theoretical and experimental resolutions" in "Physical Chemistry Chemical Physics" vol. 10, 2008, pp. 2894-2909;
[6] M. Aidelsburger et al. "Single-electron pulses for ultrafast diffraction" in "Proceedings of the National Academy of Sciences of the United States of America" vol. 107, 2010, pp. 19714-19719;
[7] A. Gliserin et al. "Compression of single-electron pulses with a microwave cavity" in "New Journal of Physics" vol. 14, 2012, p. 073055;
[8] J. Urata et al. "Superradiant Smith-Purcell emission" in "Physical Review Letters" vol. 80, 1998, pp. 516-519;
[9] G. Doucas et al. "1st Observation of Smith-Purcell Radiation from Relativistic Electrons" in "Physical Review Letters" vol. 69, 1992, pp. 1761-1764;
[10] A. Gover et al. "A Unified Theory of Magnetic Bremsstrahlung, Electrostatic Bremsstrahlung, Compton-Raman Scattering, and Cerenkov-Smith-Purcell Free-Electron Lasers" in "IEEE Journal of Quantum Electronics" vol. 17, 1981, pp. 1196-1215;
[11] G. Adamo et al. "Tuneable electron-beam-driven nanoscale light source" in "Journal of Optics" vol. 12, 2010, pp. 024012-024017;
[12] G. Adamo et al. "Electron-Beam-Driven Collective-Mode Metamaterial Light Source" in "Physical Review Letters, vol. 109, 2012, pp. 0217401-0217406;
[13] I. A. Walmsley et al. "Characterization of ultrashort electromagnetic pulses" in "Advances in Optics and Photonics, vol. 1, 2009, pp. 308-437;
[14] G. Adamo et al. "Light Well: A Tuneable Free-Electron Light Source on a Chip" in "Physical Review Letters" vol. 103, 2009, pp. 113901-113905;
[15] N. Talebi et al. "Numerical simulations of interference effects in photon-assisted electron energy-loss spectroscopy" in "New Journal of Physics" vol. 15, 2013, pp. 053013-053028; and
[16] European Patent Application No. 13001598 (not published on the priority date of the present specification).

Electron microscopes have provided so far an efficient tool for investigating the static response of samples at high spatial resolution within the sub-nanometer scale. A transmission electron microscope (TEM) can be operated e. g. in imaging, spectroscopy and diffraction modes. Cathodoluminescence (CL) light detection is also possible in TEM. Scanning electron microscopy (SEM) is based on the collection of secondary and/or back-scattered electrons to form an image or CL to perform spectroscopy. In transmission electron microscopy, the inelastic scattering of the electrons with matter, and the in-situ measurement of the electron energy loss is a powerful technique for mapping the optical density of states; this technique is called low-loss electron energy-loss spectroscopy (EELS).

In addition to static imaging of samples to be investigated and optical density of states, time-resolved spectroscopy of ultrafast processes such as chemical bonding dynamics, macromolecular conforming changes, nanomechanical vibrations, biological sample evolution, and condensed matter systems has become possible by means of conjugate electron-photon sources, with high spatial and temporal resolution [1]-[3]. In these systems, a femtosecond laser source is utilized to both excite the sample with photon pump pulses and to drive an photoemission electron source. The photoemission electrons are then focused onto the sample using static lenses and apertures, to minimize the temporal dispersion due to the space-charge effect and electron-pulse dispersion in vacuum. Setting a series of delays between the incoming electron probe pulse and photon pump pulse by means of an optical delay line, the electrons probe the dynamics of the structural processes with respect to the time reference set by the laser excitation. The time-resolution in electron microscopes is then limited by the electron pulse duration, which is intrinsically controlled by several factors, as described below. Furthermore, the conventional techniques have disadvantages in terms of controllability and structural complexity of the optical delay line for adjusting the delay between the electron probe pulse and photon pump pulse.

Mapping the structural dynamics in ultrafast electron microscopy, diffraction and spectroscopy is achieved by accumulation of several electrons detected at the detector. In order to study irreversible processes, a single pulse containing at least $10^7$ electrons is required to acquire a spectrum or an image with tolerable signal-to-noise ratio, which is referred to as a single shot operating mode in ultrafast electron diffraction and femtosecond electron diffraction [3] methodologies. Incorporating such a dense electron pulse, temporal resolution of the electron pulses at the instance of arrival at the sample is controlled at best within the picosecond regime, due to space-charge effects [3].

Avoiding the space-charge effect by operating the electron microscopes in single-electron-pulse mode is considered as an efficient way to increase the temporal resolution to 150 femtosecond, at best [4, 5]. In this mode accumulation of $10^7$-$10^9$ single-electron pulses is required at the detector, depending on the thickness of the sample. Each individual electron then forms an individual point on the screen, similar to Young's double-slit interferometer. In such a concept, the effective time-resolution is dictated by the temporal broadening of the laser beam impinging on the photoemission cathode ($\tau_{laser}$) the geometry of the cathode, temporal broadening due to the applied acceleration voltage ($\tau_{acc}$), (temporal dispersion in the vacuum ($\tau_{dis}$), and time-jitter ($\tau_{jitter}$). The latter term is due to the stochastic arrival time of the single-electron pulses on the sample in comparison with the laser clock. This term is not present in the single-shot operational mode. While the quantum behaviour of individual electron pulses, describable by the Schrödinger equation, is responsible for the longitudinal coherence length of the electron pulses, the effective pulse duration is determined by both the quantum nature and the stochastic nature of the electron pulses. The full temporal resolution of the electron pulses are then described by $\tau^2 = \tau_Q^2 + \tau_{jitter}^2$, in which $\tau_Q^2 = \tau_{laser}^2 + \tau_{disp}^2 + \tau_{acc}^2$, assuming homogeneous Gaussian broadening for the photoemission process and free-space dispersion [6].

Most optimized electron sources in practical ultrafast electron microscopes offer a temporal resolution of hundreds of femtoseconds, while the temporal coherence is only of the orders of few femtoseconds (about 8 fs) [4]. One can conclude that only a small degree of temporal coherence is present in the series of single-electron pulses as a stochastic assembly, mainly due to the presence of the time-jitter (about 6%). In such a case each electron can only temporally interfere with its own field.

Although the previously mentioned temporal resolution is sufficient for studying many physical dynamics such as nuclear motions in chemical reactions, investigation of electron motions and recombination dynamics demand subfemtosecond temporal resolution. There have been several proposals to reach the mentioned temporal resolution provoking the concept of a temporal lens. Static solutions for electron pulse compression cannot go further beyond the initial resolution of the electron pulses leaving the photoemission cathode. The few-femtosecond regime is shown to be addressable with electromagnetic compression techniques, either in the form of optical gratings or microwave cavity. However, still the time reference set by the arrival time of the laser in comparison with the electron arrival time is limited by the choice of the synchronization technique between the compressive electron-optical element and the laser source, and even a clear statement on the possible final limit on the temporal resolution due to the time jitter is not present in the literature, mainly because of the lack of theoretical models [7].

Although the single-electron mode in comparison with the single-shot mode has offered a better temporal resolution due to the omission of the space-charge effect, still the single electron mode suffers from the stochastic behaviour of the assembly of at least $10^7$ individual electron pulses needed to carry out the experiment, in comparison with the time reference set by the laser pump illuminating the sample. There is an interest in providing an improved time-reference avoiding the influence of this stochastic behaviour.

OBJECTIVE OF THE INVENTION

The objective of the invention is to provide an improved method of time-resolved pump-probe electron microscopy being capable of avoiding limitations and disadvantages of conventional techniques. In particular, the objective of the invention is to provide the method of time-resolved pump-probe electron microscopy having improved reproducibility and/or controllability of the temporal relationship of the pump and probe pulses and/or allowing reduced structural complexity of the electron microscopy apparatus used. Furthermore, the objective of the invention is to provide an improved electron microscopy apparatus for time-resolved pump-probe electron microscopy, avoiding limitations and disadvantages of conventional techniques and in particular allowing investigations with improved reproducibility and/or controllability and having a reduced structural complexity.

SUMMARY OF THE INVENTION

The above objectives are solved by a method, an electron microscopy apparatus and a sample supply device for an electron microscopy apparatus of the invention.

According to a first aspect of the invention, the above objective is solved by the general technical teaching of providing a method of time-resolved pump-probe electron microscopy, wherein a sample to be investigated is irradiated with a photonic pump pulse (or: photonic reference pulse) and with an electron probe pulse, wherein the photonic pump pulse and the electron probe pulse have a mutual temporal relationship, in particular time delay relative to each other. The photonic pump pulse is directed on a pump pulse path from a photonic source to the sample, and the electron probe pulse is directed on an electron pulse path from an electron pulse source to the sample. A sample response to the electron probe pulse, in particular a modified spatial or temporal distribution of the electron probe pulse and/or a photonic emission of the sample, is detected with a detector device. According to the invention, the photonic pump pulse is created with a photonic lattice structure being arranged adjacent to the electron pulse path. The photonic lattice structure (or: electron-driven photon source, EDPhS) has an exposed lattice surface extending along to the electron pulse path, in particular parallel to the electron pulse path. The photonic lattice structure is arranged with a distance between the exposed surface thereof and the electron pulse path, wherein the distance is selected such that the electron probe pulse is capable to pass the photonic lattice structure, while the outer edges of the electron probe pulse have a grazing contact with the photonic lattice structure. An interaction of the electron probe pulse with the photonic lattice structure is effected resulting in the creation of the photonic pump pulse.

According to a second aspect of the invention, the above objective is solved by the general technical teaching of providing an electron microscopy apparatus, which is adapted for time-resolved pump-probe electron microscopy. The electron microscopy apparatus comprises a photonic source, which is adapted for irradiating the sample with a photonic pump pulse being directed on a pump pulse path from the photonic source to the sample, an electron pulse source, which is adapted for irradiating the sample with an electron probe pulse being directed on an electron pulse path from the electron pulse source to the sample, and a detector device being adapted for detecting a sample response to the electron probe pulse. According to the invention, the photonic source comprises a photonic lattice structure being arranged adjacent to the electron pulse path and being adapted for creating the pump pulse by an interaction of the electron probe pulse with the photonic lattice structure.

According to a third aspect of the invention, the above objective is solved by the general technical teaching of providing a sample supply device for arranging a sample in an electron microscopy apparatus, in particular according to the above second aspect of the invention. The sample supply device comprises a sample holder for arranging the sample in an electron probe path of the electron microscopy apparatus, a photonic lattice structure, and a support structure carrying the sample holder and the photonic lattice structure. The photonic lattice structure is adapted for an interaction of with the electron probe pulse and the creation of a photonic pump pulse. At least one of the sample holder and the photonic lattice structure is movable relative to the support structure, so that a distance between both components can be adjusted. Preferably, the sample supply device further comprises a manipulating and actuating unit being arranged for adjusting the distance between the sample holder and the photonic lattice structure.

As a main advantage of the invention, the photonic pump pulse is created by the electron probe pulse, so that the temporal relationship of both pulses when arriving at the sample is determined. The temporal relationship is determined by geometric quantities, in particular a distance between the photonic lattice structure and the sample, a length of the pump pulse path, a velocity of the photonic pump pulse and/or a velocity of the electron probe pulse. Thus, the inventors have shown that it possible that each individual electron probe pulse imposes its own time-reference. Advantageously, the stochastic behaviour of the electron probe pulses in comparison with an external laser emission as occurring with the conventional techniques is effectively omitted.

According to the invention, a method and/or apparatus for measuring the ultrafast response of matter and systems using electron sources is provided. In contrast to the conventional methodology incorporating ultrashort laser pulses as pumps and time references (4D electron microscopy and diffraction), the invention shows the possibility of a pump-probe method without utilizing a laser source. By introducing the photonic lattice structure, i. e. a structure capable of producing coherent pulse-shaped optical fields in interaction with the arriving electron, and focusing the generated pulse-shaped optical field into the structure, the sample is pumped into a dynamical evolution. The arriving electron is then used to probe the sample at a certain delay with respect to the incident photons on the sample.

Advantageously, an electron-photon pump-probe experimental setup is obtained, which can be driven by only individual electron sources, without any laser illumination. Furthermore, with this setup the statistical distribution of individual electron probe pulses is effectively omitted, since each electron imposes its own time reference. A precise temporal resolution can be obtained as short as few femtoseconds and less (if pulse compression is implemented). The term "pump-probe electron microscopy" refers to any electron microscopy technique, wherein the sample is irradiated with an electron pulse and a photon pulse having a predetermined temporal relationship relative to each other.

Generally, the temporal relationship of the photonic pump pulse and the electron probe pulse is the time difference between the peaks of the photonic pump pulse and electron probe pulse. As the velocity of the photonic pump pulse (speed of light) is larger than the velocity of the electron probe pulse, the photonic pump pulse can arrive at the sample before the electron probe pulse as it is usually requested for a pump-probe setup of time resolved microscopy. Thus, the temporal relationship of the photonic pump pulse and the electron probe pulse preferably is a positive time delay of the electron probe pulse relative to the photonic pump pulse. However, the term temporal relationship also covers a simultaneous arrival time or even a negative time delay, wherein the peak of the photonic pump pulse arrives after the peak of the electron probe pulse at the sample.

The negative time delay can be obtained with the case of extremely relativistic electrons, which allows that the electron arrives sooner at the sample than the photons. Negative time delays can be considered for any pump-probe measurement for the following reason. Since both the photonic pump pulse and the electron probe pulse have tails (some broadening in time steps), they start exciting the sample even before the peak of the excitation reaches the structure. This means that pump can still be ahead of the probe, but influencing the structure in a way that probe senses it. Depending on the practical application of the invention, the accuracy of any correlation function to be extracted e. g. from the experimental spectra can be influenced. Without the negative delay components, the Fourier transformed correlation functions would be obtained from the positive delays only. Since in principle the positive- and negative-delay parts of the spectra are not similar, this might influence the accuracy of phase recovery by only considering positive delay. Thus, negative time delay would be preferential in the purpose to characterize the phase by Fourier transform analysis with high accuracy.

In practice, the method can be conducted with one single pair of a photonic pump pulse and an electron probe pulse, or a series of pairs of a photonic pump pulse and an electron probe pulse, wherein each electron probe pulse creates its associated photonic pump pulse. Thus, according to a preferred embodiment of the invention, the steps of irradiating the sample with the photonic pump and electron probe pulses and detecting the sample response are repeated with varying time delays of the electron probe pulse relative to the pump pulse, e. g. for investigating transient dynamic processes on an atomic level.

Advantageously, multiple measures are available for adjusting the temporal relationship between the photonic pump and electron probe pulses. According to a first variant, the time delay of the electron probe pulse relative to the pump pulse can be adjusted by setting a distance between the photonic lattice structure and the sample. Typically, the distance between the photonic lattice structure and the sample is the geometric length of a straight line between both components. If the electron pulse path should deviate from this straight line, e. g. if it is designed with deflections, the distance between the photonic lattice structure and the sample is the length of the electron pulse path therebetween. Preferably, the distance between the photonic lattice structure and the sample is adjusted by shifting at least one of a support of the photonic lattice structure and a sample holder providing the sample.

Alternatively or additionally, a length of the pump pulse path can be set for adjusting the time delay, e. g. using an optical delay line. With a preferred implementation, the length of the pump pulse path can be adjusted by setting a reflective optic arranged in the pump pulse path. With a given difference of the pulse velocities, the distance and/or the pump pulse path length define the temporal delay.

As a further alternative, a velocity of the electron probe pulse can be set for adjusting the time delay. Preferably, the velocity of the electron probe pulse is adjusted by setting an acceleration voltage of the electron pulse source, e. g. in a range of 30 kV to 300 kV.

In terms of device features, the electron microscopy apparatus preferably is provided with a control device which is adapted for adjusting the time delay of the pump pulse and the electron probe pulse according to at least one of the above variants. According to the above alternatives, the control device controls a drive of the photonic lattice structure support and/or the sample holder, a voltage supply of the electron source and/or a drive of the reflective optic spanning the pump pulse path.

According to a particularly preferred embodiment of the invention, the photonic lattice structure is adapted for exhibiting the Smith-Purcell effect. To this end, the photonic lattice structure has an optical grating on a lattice surface exposed to the electron probe pulse. The optical grating is capable of creating Smith-Purcell radiation in response to an interaction with electrons. In the Smith-Purcell effect, the emission from an electron interacting with an individual unit-cell of the optical grating, coherently interferes with the emission of the electron from the adjacent unit-cells, producing a photonic overall radiation pattern in the direction dictated by the electron velocity ($V_{el}$) and the period of the grating ($L_g$). Thus, the photonic pump pulse preferably comprises Smith-Purcell radiation created with the photonic lattice structure.

Advantageously, various variants of the photonic lattice structure are available, which have particular advantages for the inventive creation of photonic pump pulses. For instance, the photonic lattice structure can be arranged on one single side of the electron pulse path only. This embodiment offers advantages in providing a free space on an opposite side of the electron pulse path relative to the photonic lattice structure, wherein this free space can be used for arranging reflective optics for shaping the pump pulse path. Alternatively, the photonic lattice structure can be arranged on multiple sides of the electron pulse path, e. g. surrounding the electron pulse path, thus in particular increasing the efficiency of the pump pulse creation.

According to a further preferred embodiment of the invention, the photonic lattice structure comprises a slab structure (multilayer composite structure) made of different materials subsequently arranged adjacent to the electron pulse path. Advantageously, the slab structure is a compact component with at least one plane surface along the stacking direction of the different materials, which provides the lattice surface. In particular, the slab structure may comprise a photonic crystal, which allows a beam shaping and/or adjusting the direction of the photonic pump pulses. With a further alternative, the photonic lattice structure can be made of an optical metamaterial having a negative refractive index. This offers further degrees of freedom for beam shaping and/or adjusting the direction of the photonic pump pulses.

According to a further advantageous embodiment of the invention, the photonic pump pulse is focussed onto the sample with a focussing optic arranged in the pump pulse path. Focussing increased the light intensity and efficiency of the pump process at the sample. Preferably, a focussing optic comprising reflective components, like curved mirrors is used. With a particularly preferred variant, the focussing optic comprises a parabolic mirror device, preferably made of one or two parabolic mirrors, having a first focal point and a second focal point, wherein the photonic lattice structure is arranged at the first focal point and the sample is arranged at the second focal point.

According to preferred applications of the invention the detected sample response to the electron pulse irradiation comprises an energy loss spectrum of the sample, a CL signal of the sample, a diffraction pattern of the sample, or a bright-field or dark-field image of the sample. The output of the system can be e. g. either a direct measurement of the electron energy loss and electron diffraction, or the CL. If the detected sample response comprises the energy loss spectrum of the sample or the diffraction pattern of the sample, a phase characteristic of the sample response can be detected, wherein the phase characteristic is the phase of the electron wave function by passing through the sample, relative to the pump phase. Advantageously, an electron-photon pump-probe experimental setup is proposed which can be used as a holography technique with the interference fringes visible in time-energy space, in analogy to the conventional holography techniques which are based on the interference fringes in space-momentum map. The presented methodology can offer higher energy and temporal resolutions with respect to the conventional electron microscope, as discussed in [15].

In summary, the present invention considers a whole electron microscope setup, able of generating, guiding, and focusing pulsed electrons onto a sample, wherein the electron source is operated e. g. conventional photo-emission, field emission or thermionic electron guns, and static lenses, sample holders and detectors are used. In addition to the electron microscope setup and in order to facilitate time-resolved experiments, an electron-driven optical source (photonic lattice structure) is proposed by the invention. The ability of time-resolved experiments preferably is provided via changing the effective path between the electron-driven optical source and the sample, as a series of experiments. In other words, instead of imposing a laser pump source to provide the time-reference for the electron probes, in the present invention each individual electron imposes its own time reference by interacting with the electron-driven optical source. In this regard, to trigger the dynamical response of the sample in interaction with the incident photons, the response of the electron-beam driven optical source is considered as pre-knowledge, analogous to the current state-of-the-art laser-driven pump experiments in which the time response of the laser is known. A computing facility is then used to calculate the response of the sample in each step by means of a de-convolution algorithm, such as interferometry techniques.

BRIEF DESCRIPTION OF THE DRAWINGS

Further details and advantages of the invention are described in the following with reference to the attached drawings, which show in:

FIG. 7: illustrations of a sample supply device according to an embodiment of the invention;

FIG. 8: a detailed illustration of a further embodiment of an electron microscopy apparatus according to the invention being adapted for collecting CL signals;

DESCRIPTION OF PREFERRED EMBODIMENTS

Features of preferred embodiments of the invention are described here with particular reference to the creation of photonic pump pulses in an electron microscope using a photonic lattice structure. Details of the electron microscope and the operation thereof, the sample preparation and the signal processing and analysis are not described as far as they are known as such from conventional techniques. Exemplary reference is made to methods of time-resolved pump-probe electron microscopy. It is emphasized that the invention is not restricted to these examples, but rather can be used with other applications combining electron irradiation and photonic irradiation at a sample as well.

According to a preferred embodiment of the invention, the Smith-Purcell effect is used for creating a photonic reference pulse at a defined flexible reference time, which is independent of the stochastic behavior of a single-electron probe pulse for investigating a sample. The Smith-Purcell emission process is due to an interaction of the electron with the field of its own scattered at an optical grating, so that a perfect time reference is set which is dictated only by electron velocity ($V_{el}$) and the period of the grating ($L_g$), regardless of the stochastic behavior of the individual electron probe pulses. This makes it observable even with field-emission and thermal electron sources in state-of-the art transmission electron microscopes ([8] and [9]).

The travel time of each individual electron between two adjacent unit-cells of the optical grating is $$\Delta t_{el} = L_g / V_{el}$$

while for the emitted photons it is $$\Delta t_{ph} = \frac{L_g}{c}\cos(\theta) + \frac{mh}{E_{ph}}$$

where c is the velocity of light in free space, $\theta$ is the angle of the radiated beam with respect to the axis of the grating, m is the diffraction order from the grating, h is the Planck constant, and $E_{ph}$ is the energy of the emitted photons. In such a way the delay between the electrons and photons to travel from one element of the grating to the adjacent element is $$\tau = \Delta t_{el} - \Delta t_{ph}.$$

Imposing the phase-matching criteria between the electrons and the emitted photons by $\tau=0$, a strong radiation will be emitted at an angle $\theta$, due to the constructive interference of the individual photons generated at each unit cell. In this concept, the electron imposes its own time-reference according to the distance between the grating elements and electron velocity, while the geometry and material structure of the individual elements imposes the conditions on the energy of the emitted photons.

Figure 1:
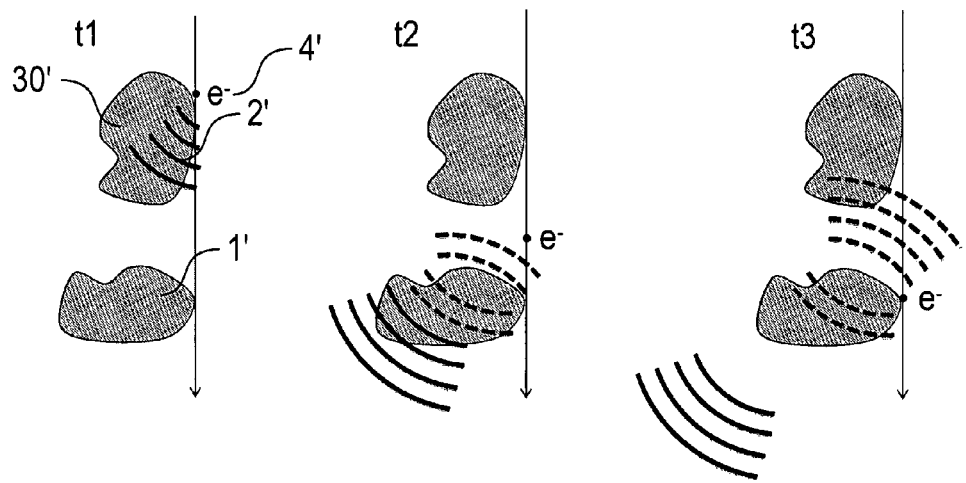
FIG. 1: a schematic illustration of the Smith-Purcell effect used according to the invention for creating a photonic time reference for an electron pulse.

FIG. 1 schematically illustrates a process in which an electron 4' (individual one electron pulse) is interacting with a system composed of two coupled structures 30', 1' (two interaction points). $t_1$, $t_2$, and $t_3$ show the times at which the electron 4' arrives at the first interaction point and emits some photons 2' ($t_1$), the photons 2' reach the second structure 1' and pump it to a certain photonic state ($t_2$), and the electron 4' arrives at the second structure 1' and probes the previously pumped state at a delay $\tau$ with respect to the pump arrival time at the structure 1' ($t_3$).

With further details, at time $t_1$ the electron 4' is in the vicinity of the first structure 30', interacting with it in an inelastic way, which results in the Smith-Purcell effect based generation of some photons 2' with the energy of $E_{ph}^{(1)}$. The generated photons 2' travel faster in free-space than the electrons 4', and reach the second structure 1' at time $t_2 = t_1 + L/c$, where L is the distance between the two interaction points. The second structure 21' then emits scattered light at the same photon energy, and is initially pumped into the higher photonic state. The electron 4' arrives at the second interaction point at time $t_3 = t_1 + L/V_{el}$, and probes the initially created photonic state of the second structure. In this design the delay $\tau$ between the pump and probe at the second interaction point is $$\tau = \frac{L}{V_{el}} - \frac{L}{c} = \frac{L}{V_{el}}(1 - \beta_{el})$$

where $\beta_{el} = V_{el}/c$. In this regard, the delay between the photons and electrons is only dictated by the electron velocity and the distance between the two interaction points, regardless of the stochastic time-jitter parameter. That means that each individual electron 4' imposes its own time-frame. Examples of the photonic radiation mechanism are the Smith-Purcell light source ([10]), or metamaterials ([11], [12]) interacting with electrons.

For using this process in time-resolved microscopy, e. g. spectroscopy or diffraction techniques, the first interaction point in FIG. 1 is substituted with a photonic lattice structure 30 and the second interaction point in FIG. 1 is substituted with the sample 1 to be investigated. This is shown in FIG. 2, which schematically illustrates a first embodiment of the inventive electron microscopy apparatus 100.

Figure 2:
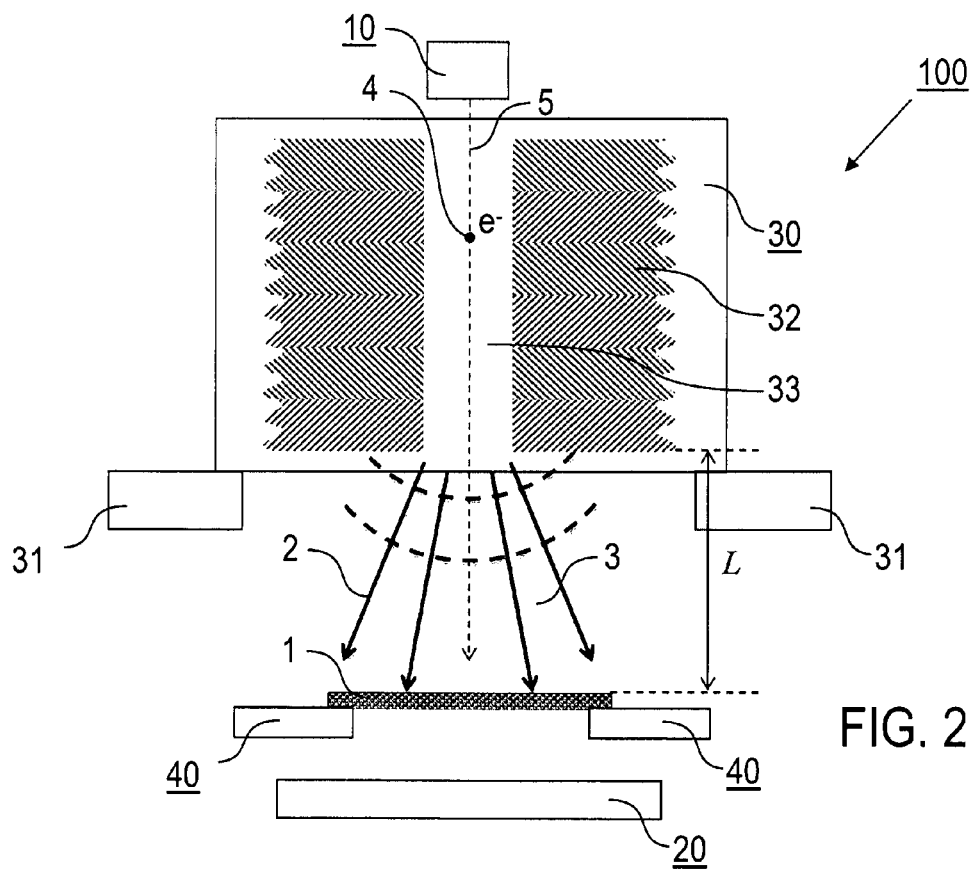
FIG. 2: a schematic illustration of a first embodiment of an electron microscopy apparatus according to the invention.

The electron microscopy apparatus 100 of FIG. 2 comprises an electron pulse source 10, a photonic lattice structure 30, a sample holder 40 and a detector device 20. These components are arranged in an evacuated environment, e. g. in an electron microscope column, and they are connected with further supply devices and control devices (not shown in FIG. 2). Supply devices are adapted e. g. for supplying an acceleration voltage to the electron pulse source 10, while control devices are arranged, e. g. for position control of the photonic lattice structure 30 and/or the sample holder 40 or for collecting sample response signals with the detector device 20.

The electron pulse source 10 comprises e. g. a photoemission source including a photocathode and an anode (not shown in detail). In response to an irradiation with a fs laser pulse, a photoelectron is created at the photocathode and accelerated to the anode by an acceleration voltage of e. g. 200 kV. The photoelectron passes the anode, e. g. by a through-hole therein, along a straight line according to the direction of acceleration between the photocathode and the anode and defining an electron pulse path 5.

The electron pulse path 5 runs through the photonic lattice structure 30 to the sample 1 on the sample holder 40. The photonic lattice structure 30 has a slab structure 32 arranged on a support 31. The slab structure 32 (details see below) has a hollow channel 33 wherein a lattice surface is exposed to the electron pulse path 5 on multiple sides thereof. Preferably, the hollow channel 33 has an inner diameter which is selected such that the electron probe pulse 4 travelling on the electron pulse path 5 in the centre of the hollow channel 33 interacts with the slab structure 32 in all radial directions relative to the electron pulse path 5. With preferred examples, the distance of the electron pulse path 5 from the lattice surface is in a range of 0.01 µm to 0.5 µm.

The sample holder 40 is a mechanical stage providing the sample 1 at a predetermined distance L relative to the photonic lattice structure 30, in particular relative to the slab structure 32 thereof. Preferably, the distance L is variable, e. g. by using a movable support 31 of the photonic lattice structure 30 and/or a movable sample holder 40. The sample 1 is provided by the sample holder 40 such that the electron pulse path 5 hits the sample 1 and the sample 1 can be irradiated by electrons emitted from the electron source 10 and by a photonic pump pulse 2 emitted at the photonic lattice structure 30. The sample holder 40 can have a design like a sample carriage of a conventional electron microscope, or it can be a part of an inventive sample supply device 200 (see FIG. 7).

Figure 6:
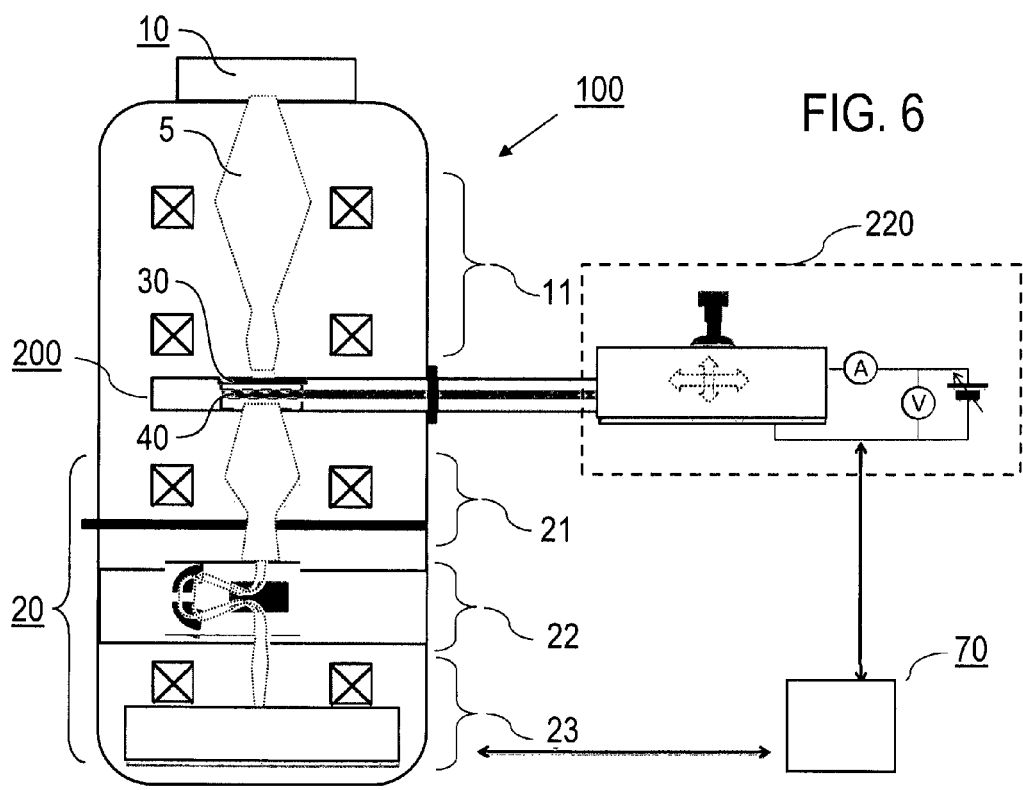
FIG. 6: a detailed illustration of a further embodiment of an electron microscopy apparatus according to the invention being adapted for collecting energy loss spectra.

The detector device 20 is configured for detecting a sample response to the electron pulse irradiation. The particular design of the detector device is selected in dependency on the sample feature to be investigated. With a preferred example, the detector device 20 comprises a semiconductor based camera for collecting transmission or diffraction images. Alternatively, other detector types can be used, e. g. as shown in FIG. 6 or 8, or multiple detector types can be combined.

The photonic lattice structure 30 is a photon-source driven by an electron probe pulse 4. It provides a grating, composed of different slabs, into which a hole is drilled for forming the hollow channel 33. The slabs may comprise any materials providing the optical radiation at the output of the structure at the desired frequency and radiation pattern. With a practical example, the slabs are made of gold and silica with a thickness of 0.1 µm in an alternating fashion. As described above, the delay between the photons and the electrons at the location of the specimen is given by $\tau=(1-\beta_{el})L/V_{el}$. For example, for an electron with the velocity $V_{el}=0.67$ c, a distance of L=10 µm results in a delay of 16.4 fs. Changing the distance L by 0.5 µm results in a step of 0.82 fs in the delay. The distance L can be accurately controlled by means of a piezoelectric actuator, e. g. in the sample holder 40, or combined piezoelectric/screw actuators (see FIG. 7) which can offer a travel range as wide as 4 mm and a fine resolution at an Angstrom level.

The electron microscopy apparatus 100 of FIG. 2 is operated for time-resolved imaging the sample 1 by the following steps. The sample 1 is positioned on the sample holder 40. The distance L between the photonic lattice structure 30 and the sample holder 1 is adjusted such that a photonic pump pulse 2 created at the photonic lattice structure 30 and traveling along a pump pulse path 3 to the sample 1 and the electron probe pulse 4 traveling along the electron pulse path 5 have a predetermined mutual temporal relationship, e. g. 1 fs, when arriving at the sample 1. After collecting a first image, the temporal relationship can be changed in a stepwise fashion, e. g. by 0.1 fs, thus collecting a series of images with different time delays. The photonic radiation from the photonic lattice structure 30 can be characterized in a pre-step using several well-advanced optical pulse characterization techniques, such as interferometry, tomography, and/or spectrographic techniques [13]. While the photonic pump pulse is characterized as a reference, the information about the sample and its dynamical evolution is triggered in microscopy, spectroscopy, and/or diffraction.

Figure 3:
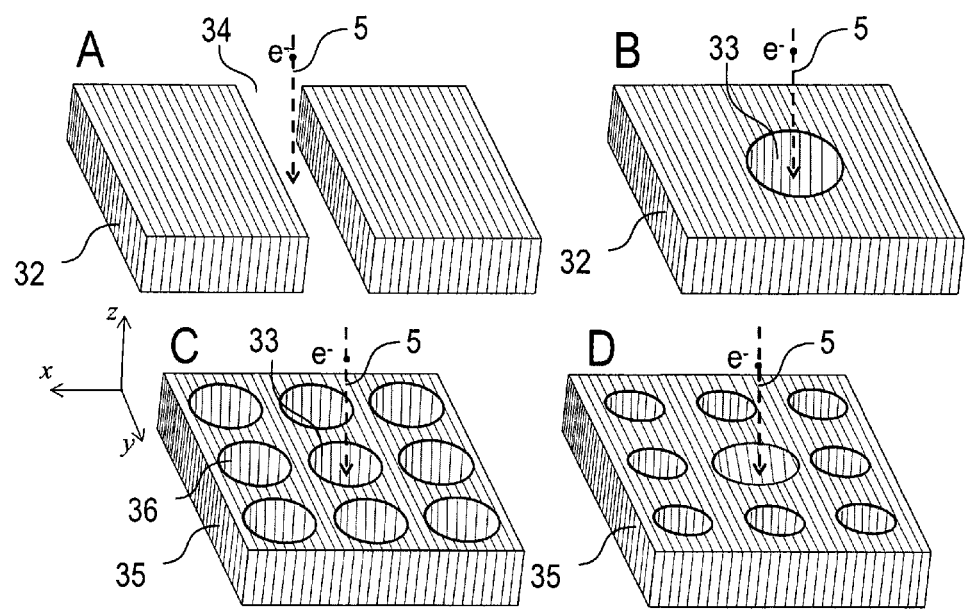
FIG. 3: schematic illustrations of photonic lattice structures used according to the invention.

FIG. 3 illustrates examples of electron-driven photonic lattice structures (EDPhSs) to be used in an inventive electron microscope apparatus. Along the vertical z-axis direction (axial direction of the electron microscope), all these sources provide a one dimensional grating composed of slabs of at least two different materials. If the mentioned slabs are much thinner than the wavelength of the emitted photons, they can be considered as composite materials.

FIG. 3A shows a slab structure 32 having a slit 34, which forms a double sided grating. The pump pulse path 5 runs parallel to the negative z-axis through the slit 34, so that an electron pulse interacts with the slab structure 32. The slit 34 has a width of e. g. 0.4 µm. According to FIG. 3B, a hole is drilled into the slab structure 32, thus forming a hollow channel 33 like in FIG. 2 (see [14]).

FIG. 3C schematically shows a multilayer photonic crystal structure 35 which can be used for beam steering of the generated photons. The photonic crystal structure 35 has a slab design like the slab structure 32 of FIG. 3B and additionally multiple channels 36 running parallel to the central hollow channel 33. The channels 36 are formed as an optical lattice so that the beam steering function is obtained by diffraction and interference of the created photons within the photonic crystal structure 35. The channels 36 can be replaced by other structures fulfilling the equal function. With a further variant, the photonic crystal structure 35 can be formed as a multilayer cavity made of a photonic crystal, which offers both the ability to steer the generated photons into a pencil-beam radiation, and also to enhance the emission probability of the single-electron beam, as shown in FIG. 3D. The field enhancement occurs due to the localization of the optical density of states inside the cavity with high quality factor, which therefore increases the field intensity and interaction probability of the field with swift electrons.

The variants of FIGS. 3C and 3D offer a wide range of applications due to the ability for steering the emitted photons into a pencil-beam radiation pattern. That is because the Bragg reflection which defines an effective band-gap for the photonic crystal restricts the emitted photons of certain energy to propagate inside the heterostructure of the one-dimensional grating laterally, and makes them to diffract from the hole towards the sample, in a pencil-beam radiation pattern. This also makes the radiation to obey the signature of the cavity modes of the photonic crystal, and being emitted in a coherent way.

Moreover, the length of the grating in z-direction has an effect on the temporal broadening of the excited photons. As a rule, the more the length of the grating, the more is the temporal broadening. It can be understood from the analysis of the diffraction grating: an infinite grating causes a continuous emission of the light by mapping the momentum of the electron to a certain diffraction order, while a single layer emits an attosecond pulse with a radiation pattern which covers a wide angular momentum, as is understood from the concept of transition radiation. With a practical example, a photonic lattice structure 30 having a length along the z-axis of 20 µm and the period of 0.2 µm is capable of creating a photonic pump pulse with a duration of 10 fs, in interaction with a relativistic electron at the kinematic energy of 200 keV.

Figure 4:
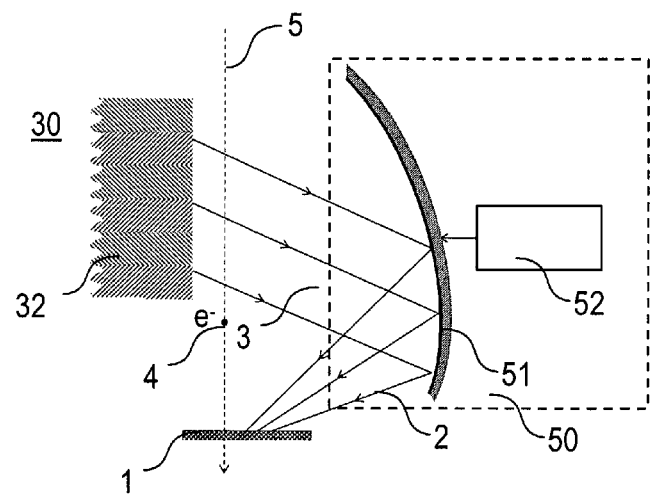
FIG. 4: an illustration of a reflective adjustable optic arranged in a pump pulse path.

As a further alternative, simple single-sided Smith-Purcell radiation may also be considered, as shown in FIG. 4, wherein the photonic lattice structure 30 is arranged on one side of the pump pulse path 5 only. On an opposite side, a reflective optic 50 is arranged, which comprises a mirror 51 and a mirror drive 52. The mirror 51 is arranged for reflecting photons created at the slab structure 32 of the photonic lattice structure 30 towards the sample 1. The position and orientation of the mirror 51 defines the length of the pump pulse path 3, which can be changed with the mirror drive 52. The reflective optic 50 provides a delay line. In the illustration, one single mirror 51 is used, which has a curved focussing surface. Alternatively, a plane surface or multiple mirrors each having a plane or a curved surface could be used.

The configuration of FIG. 4 offers a benefit over the embodiment of FIG. 2 in the precise delay control between the photons and electrons arriving at the sample 1, and also on the ability to focus the generated photons onto the sample. According to FIG. 4, the temporal delay between the photon pump pulse 2 and the electron probe pulse 4 is determined by three parameters: electron velocity $V_{el}$, the distance between the electron driven photonic lattice structure 30 $L_{el}$ and the sample 1, and the effective path length of the generated photons $L_{ph}$ on the pump pulse path 3. The temporal delay is then given by $$\tau = \frac{L_{el}}{V_{el}} - \frac{L_{ph}}{c} = \frac{L_{el}}{V_{el}}\left(1 - \beta_{el}\frac{L_{ph}}{L_{el}}\right).$$

It is possible to match the arrival time of photons and electrons, by setting $\beta_{el} = L_{el}/L_{ph}$, and even to go to negative delays by setting $\beta_{el}L_{ph} > L_{el}$. Negative delays would be preferential in the purpose to characterize the phase by Fourier transform analysis with high accuracy.

Figure 5:
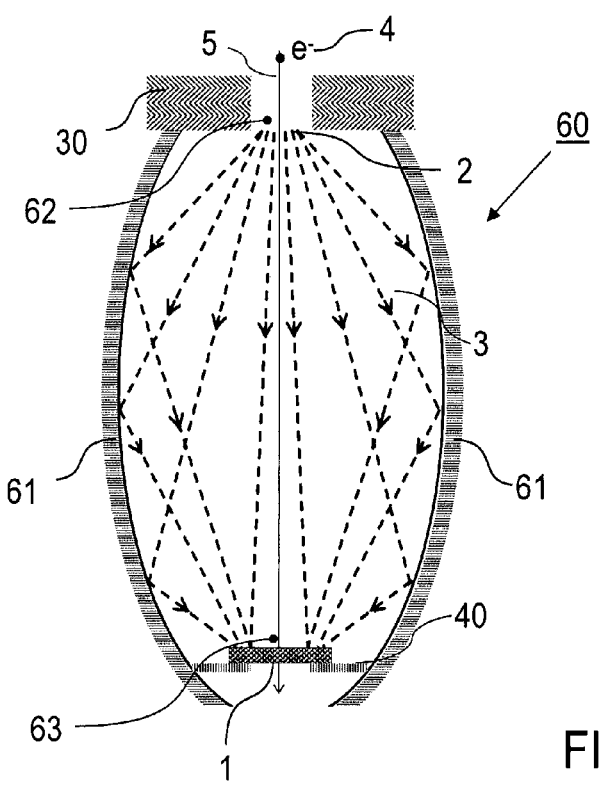
FIG. 5: an illustration of a reflective focusing optic arranged in a pump pulse path.

In another embodiment, the photonic lattice structure 30 and the sample holder 40 are arranged inside a focussing optic 60 as shown in FIG. 5. This embodiment has advantages for obtaining further control over the mutual coherence of the electron probe pulse 4 and the photon pump pulse 2. The focussing optic 60 comprises an optical ellipsoidal cavity made of parabolic mirrors 61, which define first and second focal points 62, 63. The photonic lattice structure 30 and the sample holder 40 with the sample 1 are positioned at the first and second focal points 62, 63, respectively. In this configuration, the generated transmitted photons of the photon pump pulse 2 advantageously will reach the sample 1, regardless of the radiation pattern of the photonic lattice structure 30.

FIG. 6 illustrates a further embodiment of the inventive electron microscopy apparatus 100 with more details. The electron microscopy apparatus 100 is a transmission electron microscope (TEM) equipped with an EELS system to perform ultrafast electron microscopy (see FIG. 9), and/or time-energy holography (see FIG. 10). The electron source 10 comprises a photoemission source as described with reference to FIG. 2. Condenser lenses and apertures 11 shape the electron pulse path 5 towards the photonic lattice structure 30 and the sample at the sample holder 40. An objective lens and aperture 21, an energy selecting filter 22 and a projection and detection unit 23 of the detector device 20 are arranged downstream of the sample holder 40. The detector device 20 is connected with a control device 70, e. g. a micro-computer, including a memory and an analyzing and processing unit.

Both of the photonic lattice structure 30 and the sample holder 40 are components of a sample supply device 200, which is provided with an external manipulating and actu-ating unit 220. The photonic lattice structure 30 has a fixed position above the sample holder 40. The sample holder 40 can be manipulated with the actuating and manipulating unit 220, e. g. with a 3-axis tubular system, to be able to precisely control the sample position relative to the photonic lattice structure 30 and the electron pulse path 5. To this end, the actuating and manipulating unit 220 is connected with the control device 70.

The sample supply device 200, as shown with further details in FIG. 7, represents an independent subject of the present invention. FIG. 7A shows a cross-sectional side view (perpendicular to the z-axis and the electron pulse path 5), while FIG. 7B shows a cross-sectional top view along the electron pulse path 5) of the sample supply device 200 with a support structure 210 carrying the photonic lattice structure 30 and the sample holder 40, and with the actuating and manipulating unit 220. As an important advantage of the invention, the sample supply device 200 of FIG. 7 can be used as a modification of a conventional transmission electron microscope.

The support structure 210 comprises a main body 211 accommodating a carrier rod 212, which is movable relative to the main body 211. The main body 211 has a longitudinal extension, which is oriented perpendicular relative to the axial direction (z-axis) of the electron microscope. An O-ring 213 is used for holding the main body 211 in a sealed fashion in a wall or a vacuum flange of the electron microscope column (not shown). The photonic lattice structure 30 is fixedly connected with a distal end of the main body 211, while the sample holder 40 is fixed at the movable carrier rod 212. Accordingly, by moving the carrier rod 212 with the actuating and manipulating unit 220, the distance of the sample holder 40 relative to the photonic lattice structure 30 can be set, and the radial position of the sample relative to the electron pulse path 5 can be adjusted.

The actuating and manipulating unit 220 is a three-dimensional nanorobotic manipulation system which can be controlled by the control device 70. It comprises a microstage actuator 221, an x-y drive 222, and a power supply 223 for the microstage actuator 221. The microstage actuator 221 preferably is adapted for fine translations of the carrier rod 212 along the z-axis and in a plane perpendicular to the z-axis, e. g. using piezoelectric actuators. The x-y drive 222 preferably is adapted for coarse translations of the carrier rod 212 in a plane perpendicular to the z-axis, e. g. using a manually driven screw.

FIG. 8 illustrates a further embodiment of the inventive electron microscopy apparatus 100. The electron microscopy apparatus 100 is a scanning electron microscope (SEM) which is adapted for collecting cathodoluminescence (CL) signals created by the sample 1 in response to an electron irradiation, and/or for time-energy holography measurements. An electron probe pulse created with the electron source 10 is imaged along the electron pulse path 5 by a condenser lens 11 through the photonic lattice structure 30 to the sample 1. The photonic lattice structure 30 is fixed on a support 31, which is connected to the wall of the electron microscope column. The electron microscope column can be equipped with an aperture for removing or replacing the photonic lattice structure 30. Furthermore, the support 31 can be provided with a drive unit (not shown), so that the photonic lattice structure 30 can be moved relative to the sample holder 40. The detector device 20 comprises a CL collection and detection system, including a mirror 24, an imaging optic 25 and a sensor 26, which is connected with the control device 70.

The embodiment of FIG. 8 can be used as a system for performing time-energy holography with the SEM equipped with the CL detection system. In fact the sample stage in SEM is larger in comparison with TEM, and therefore design of the sample supply device is also easier. A modified sample supply device is used, which is connected with the wall of the electron microscope column. The sample holder 40 is carried and manipulated with an external manipulating and actuating unit 220, which allows a three-dimensional control over the sample position and which is connected with the control device 70.

Figure 10:
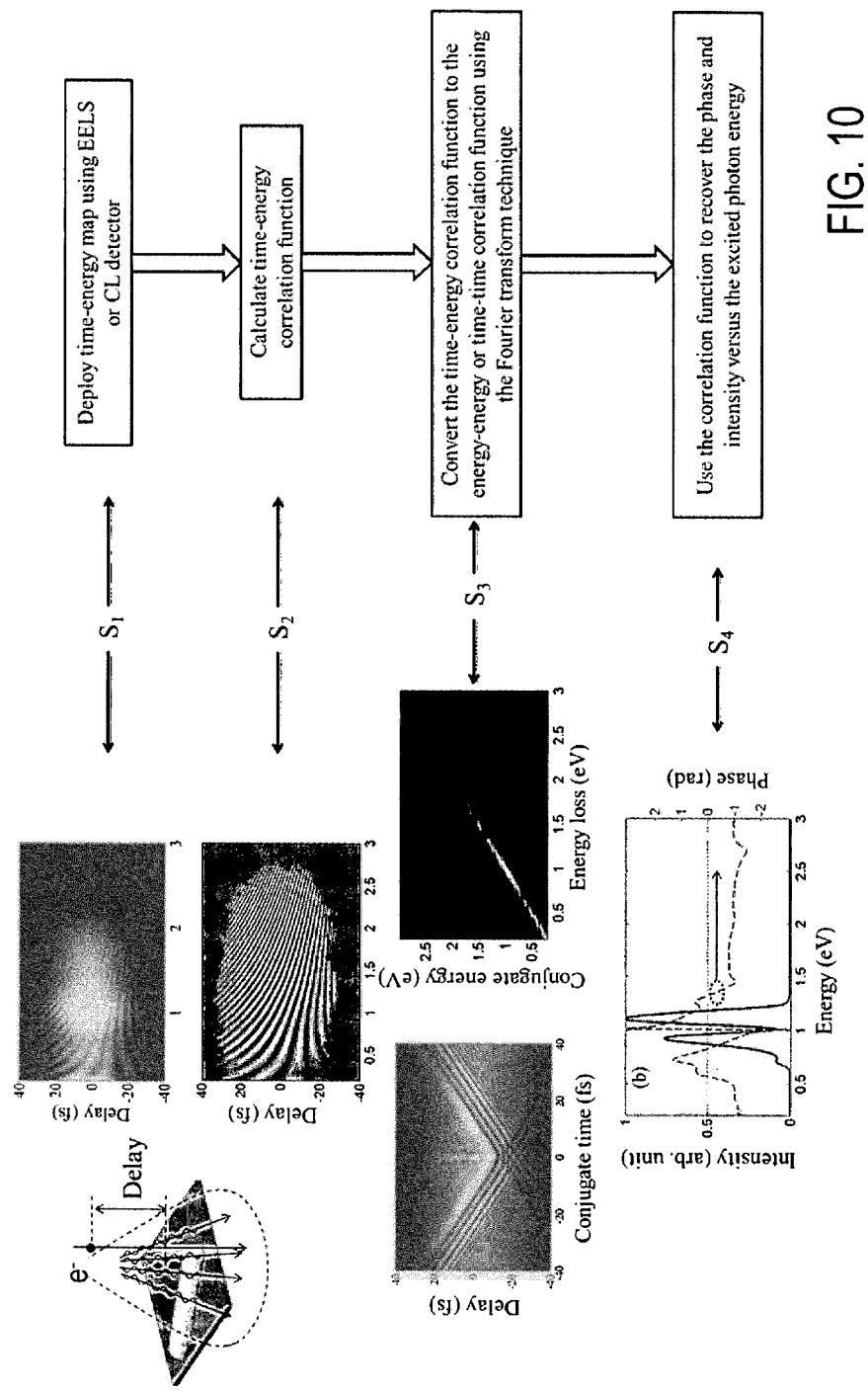
FIG. 10: an application of the invention for measuring time-energy holography with an electron microscope.

It is noted that the control device 70, including processing and memory units, introduced in both embodiments of FIGS. 6 and 8 is used for acquiring and saving the sample response, e. g. the EELS or CL data, for controlling the actuators of a manipulating and actuating unit 220, and optionally for performing phase recovery as described in the time-energy holography technique (see FIG. 10).

Figure 9:
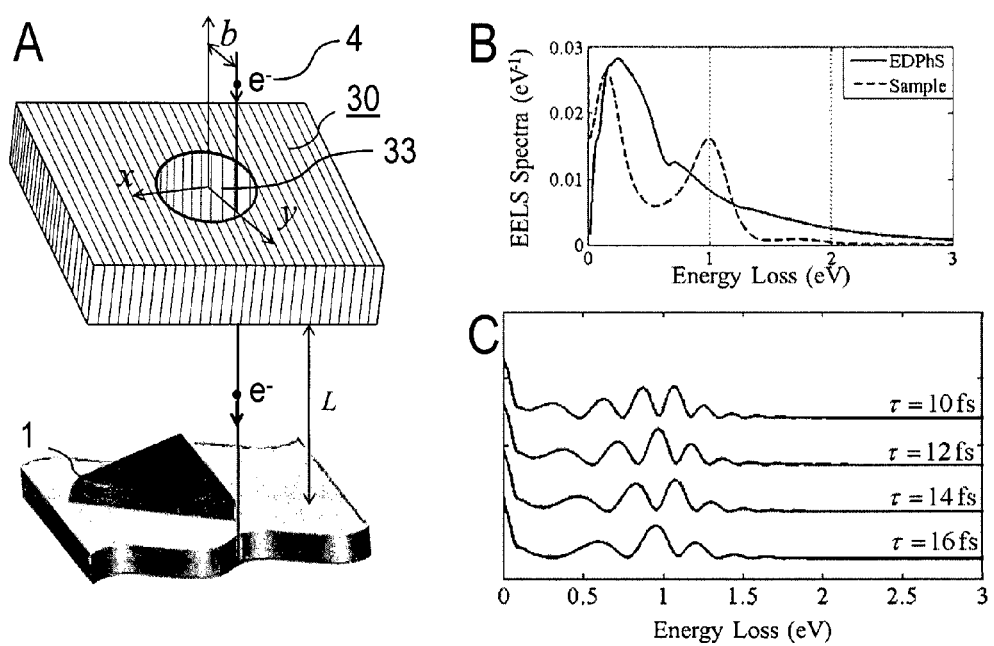
FIG. 9: an application of the invention for measuring energy loss spectra.

FIG. 9 illustrates an application of the invention for investigating a sample 1 comprising a triangular gold nano-prism with a thickness of 40 nm and an edge length of 400 nm, positioned upon a $Si_3N_4$ substrate with a thickness of 30 nm. The photonic lattice structure 30 comprises a multilayer slab structure composed of 11 layers of gold and silica each with the thickness of 200 nm, starting with a gold layer at the lowest position. A hollow channel 33 with a diameter of 700 nm is drilled into the structure, and an electron probe pulse 4 at the energy in a range of 40 keV to 200 keV is passed through the hollow channel 33 at the impact of b=280 nm (FIG. 9A). The initial distance of the photonic lattice structure 30 and the sample 1 is e. g. 1.8 μm and is changed to 8.6 μm step by step, corresponding to the delays between 10 and 50 fs, respectively.

EELS spectra have been calculated using a finite-differentiation numerical code described in [15] and [16]. The calculated EELS spectra for the sample 1 and the photonic lattice structure 30 are depicted in FIG. 9B, and the overall calculated EELS map in the time-energy space is depicted in FIG. 9C. A clear interference pattern is demonstrated in FIG. 9C, which is due to the constructive and destructive interference of the scattered photons due to the photonic lattice structure 30 and the scattered photons due to the electron probe pulse interacting with the sample 1.

In analogy to the inline spectroscopy technique, the methodology proposed here can increase the visibility of the interference fringes. The interference fringes formed here are also visible in the EELS signal, as proposed in ref. [15]. However, in order to observe the interference fringes in the conventional ultrafast electron microscopes, the electron waves should have a high degree of mutual coherence with the incorporated laser beams, which is not possible to achieve due to the time-jitter of the electron probe pulses with respect to the laser as a spectroscope. With the present invention, the interference fringes have a higher visibility due to the omission of the time-jitter phenomenon.

The preserved mutual coherence and exploited interference patterns allows to recover the phase data of the spectrum, for example EELS spectra, by incorporating an interferometry technique. This technique is referred to here as the time-energy holography, which is illustrated in FIG. 10. At the first step, the EELS map ($\Gamma^{EELS}(\hbar\omega,\tau)$, in which $\hbar\omega$ is the energy of the excited photons, and $\tau$ is the delay between pump and probe) will be recorded by considering fine delay steps, which makes the interference pattern visible. It can be achieved by considering the Nyquist rate in signal processing algorithms. As an example here, the computed EELS map for an electron trajectory passing through the corner of a gold nanoprism is considered (FIG. 9, $S_1$). In fact, the EELS signal has contributions from the induced field caused by the interaction of electron with both EDPhS and sample. In weak interaction regimes it can be written as [15]:

$$\Gamma^{EELS}(\hbar\omega, \tau) = \frac{1}{4}\left(\frac{q}{\hbar\omega}\right)^2 \left|\tilde{\tilde{E}}_z^{(sample)}\left(\hbar\omega; k_z = \frac{\omega}{V}\right) + e^{i\omega\tau}\tilde{\tilde{E}}_z^{(EDPhS)}\left(\hbar\omega; k_z = \frac{\omega}{V}\right)\right|^2 =$$

$$\frac{1}{4}\left(\frac{q}{\hbar\omega}\right)^2 \left|\tilde{\tilde{E}}_z^{(sample)}(\hbar\omega)\right|^2 +$$

$$\frac{1}{4}\left(\frac{q}{\hbar\omega}\right)^2 \left|\tilde{\tilde{E}}_z^{(EDPhS)}(\hbar\omega)\right|^2 \frac{1}{2}\left(\frac{q}{\hbar\omega}\right)^2 \text{Re}\left\{\tilde{\tilde{E}}_z^{(sample)}(\hbar\omega)\tilde{\tilde{E}}_z^{*(EDPhS)}(\hbar\omega)e^{-i\omega\tau}\right\}$$

In which, $\tau$ is the delay between photonic pump pulse and the electron probe pulse, $\tilde{\tilde{E}}_z^{(\cdot)}(\omega;k)$ is the Fourier transform of the induced electric field in frequency-momentum space, $\omega$ is the angular frequency of the excited photons, q is the electron charge, and V is the electron velocity. One can perform an experiment in which only the photonic lattice structure 30 is considered. This will result in:

$$\Gamma_{ref}^{EELS}(\hbar\omega) = \frac{1}{4}\left(\frac{q}{\hbar\omega}\right)^2 \left|\tilde{\tilde{E}}_z^{(EDPhS)}(\hbar\omega)\right|^2$$

which is considered as a reference signal to be used in the holography technique. Using these two data a correlation function can be constructed as $$C(\hbar\omega;\tau) = -1 + \Gamma^{EELS}(\hbar\omega,\tau)/\Gamma_{ref}^{EELS}(\hbar\omega)$$

which is shown in FIG. 10 ($S_2$). This correlation function can be then used to extract the phase of the spectra. In order to proceed, the energy-time correlation function is converted to two-energy or a two-time correlation function, using the Fourier transform, as:

$$C(\tau'; \tau) = \int_{-\infty}^{+\infty} C(\omega; \tau) e^{-i\omega\tau'} d\omega$$

or $$C(\hbar\Omega; \hbar\omega) = \int_{-\infty}^{+\infty} C(\hbar\omega; \tau) e^{-i\Omega\tau} d\tau$$

Both correlation functions are shown in FIG. 10 ($S_3$). In the case of a broadband spectrum, energy-energy correlation function is more suitable for phase recovery. The two energy correlation function can be written as:

$$\tilde{C}(\hbar\Omega; \hbar\omega) = \left|\tilde{\tilde{E}}_z^{(sample)}\left(\hbar\omega, k_z = \frac{\omega}{V}\right)/\tilde{\tilde{E}}_z^{(EDPhS)}\left(\hbar\omega, k_z = \frac{\omega}{V}\right)\right|^2 \delta(\Omega) +$$

$$\left(\tilde{\tilde{E}}_z^{(sample)}\left(\hbar\omega, k_z = \frac{\omega}{V}\right)/\tilde{\tilde{E}}_z^{(EDPhS)}\left(\hbar\omega, k_z = \frac{\omega}{V}\right)\right)\delta(\omega - \Omega) +$$

$$\left(\tilde{\tilde{E}}_z^{(sample)}\left(\hbar\omega, k_z = \frac{\omega}{V}\right)/\tilde{\tilde{E}}_z^{(EDPhS)}\left(\hbar\omega, k_z = \frac{\omega}{V}\right)\right)^*\delta(\omega + \Omega)$$

Using this correlation function, one can obtain the excited complex valued electric field as:

$$\tilde{E}_z^{(sample)}\left(\hbar\omega, k_z = \frac{\omega}{V}\right) = \tilde{E}_z^{(EDPhS)}\left(\hbar\omega, k_z = \frac{\omega}{V}\right) \times \int_0^{+\infty} C(\hbar\Omega; \hbar\omega)d\Omega =$$

$$\tilde{E}_z^{(EDPhS)}\left(\hbar\omega, k_z = \frac{\omega}{V}\right) \times \int_0^{+\infty} \int_{-\infty}^{+\infty} C(\hbar\omega; \tau)e^{-i\Omega\tau}d\tau d\Omega$$

The phase and the intensity of the Fano-type resonance for the example provided here are demonstrated in FIG. 10 ($S_4$).

The features of the invention disclosed in the above description, the drawings and the claims can be of significance both individually as well as in combination or sub-combinations for the realization of the invention in its various embodiments.

The invention claimed is:

1. A method of time-resolved pump-probe electron microscopy, comprising the steps of
   (a) irradiating a sample with a photonic pump pulse being directed on a pump pulse path from a photonic source to the sample,
   (b) irradiating the sample with an electron probe pulse being directed on an electron pulse path from an electron pulse source to the sample, wherein the photonic pump pulse and the electron probe pulse arrive at the sample with a predetermined temporal relationship relative to each other, and
   (c) detecting a sample response to the electron probe pulse irradiation with a detector device, wherein
   the photonic source comprises a photonic lattice structure being arranged adjacent to the electron pulse path, and
   the photonic pump pulse is created by an interaction of the electron probe pulse with the photonic lattice structure.

2. The method according to claim 1, wherein the steps (a) to (c) are repeated with varying temporal relationships of the electron probe pulse relative to the photonic pump pulse.

3. The method according to claim 1, wherein the temporal relationship of the electron probe pulse relative to the photonic pump pulse is adjusted by setting at least one of a distance between the photonic lattice structure and the sample, a length of the pump pulse path and a velocity of the electron probe pulse.

4. The method according to claim 3, including at least one of the features
   the distance between the photonic lattice structure and the sample is adjusted by shifting at least one of a support of the photonic lattice structure and a sample holder providing the sample,
   the velocity of the electron probe pulse is adjusted by setting an acceleration voltage of the electron pulse source, and
   the length of the pump pulse path is adjusted by setting a reflective optic arranged in the pump pulse path.

5. The method according to claim 1, wherein the photonic lattice structure has at least one of the features
   the photonic lattice structure is arranged on one single side of the electron pulse path,
   the photonic lattice structure is arranged on multiple sides of the electron pulse path,
   the photonic lattice structure comprises a slab structure made of different materials subsequently arranged adjacent to the electron pulse path,
   the photonic lattice structure comprises an optical metamaterial having a negative refractive index, and
   the photonic lattice structure comprises a slab structure of a photonic crystal.

6. The method according to claim 1, wherein the photonic pump pulse is focussed to the sample with a focussing optic arranged along the pump pulse path.

7. The method according to claim 6, wherein the focussing optic comprises parabolic mirrors having a first focal point and a second focal point, wherein the photonic lattice structure is arranged at the first focal point, and the sample is arranged at the second focal point.

8. The method according to claim 1, wherein the sample response detected with step (c) comprises
   an energy loss spectrum of the sample,
   a cathodoluminescence signal of the sample,
   a diffraction pattern of the sample, or
   a bright-field or dark-field image of the sample.

9. The method according to claim 1, wherein
   the sample response detected with step (c) comprises an energy loss spectrum of the sample or a diffraction pattern of the sample, and
   a phase characteristic of the sample response is detected with step (c), wherein the phase characteristic is the phase of the electron wave function by passing through the sample, relative to the pump phase.

10. The method according to claim 1, wherein the photonic pump pulse comprises Smith-Purcell radiation created with the photonic lattice structure.

11. An electron microscopy apparatus, configured for time-resolved pump-probe electron microscopy, comprising
    a sample holder being arranged for providing a sample,
    a photonic source being arranged for irradiating the sample with a photonic pump pulse being directed on a pump pulse path from the photonic source to the sample,
    an electron pulse source being arranged for irradiating the sample with an electron probe pulse being directed on an electron pulse path from the electron pulse source to the sample, and
    a detector device being arranged for detecting a sample response to the electron pulse irradiation, wherein
    the photonic source comprises a photonic lattice structure being arranged adjacent to the electron pulse path and being arranged for creating the photonic pump pulse by an interaction of the electron probe pulse with the photonic lattice structure.

12. The electron microscopy apparatus according to claim 11, further comprising
    a control device being arranged for adjusting a temporal relationship of the photonic pump pulse and the electron probe pulse arriving at the sample by setting at least one of a distance between the photonic lattice structure and the sample, a length of the pump pulse path and a velocity of the electron probe pulse.

13. The electron microscopy apparatus according to claim 11, including at least one of the features
    a support of the photonic lattice structure and the sample holder being movable relative to each other,
    the control device is arranged for setting an acceleration voltage of the electron pulse source,
    the pump pulse path includes a reflective optic being arranged for setting the length of the pump pulse path, and
    the pump pulse path includes a focussing optic being arranged for focussing the photonic pump pulse to the sample.

14. The electron microscopy apparatus according to claim 13, wherein
the pump pulse path includes the focussing optic, and
the focussing optic comprises parabolic mirrors having a first focal point and a second focal point, wherein
the photonic lattice structure is arranged at the first focal point, and
the sample is arranged at the second focal point.

15. The electron microscopy apparatus according to claim 11, including at least one of the features
the photonic lattice structure is arranged on one single side of the electron pulse path,
the photonic lattice structure is arranged on multiple sides of the electron pulse path,
the photonic lattice structure comprises a slab structure made of different materials subsequently arranged adjacent to the electron pulse path,
the photonic lattice structure comprises an optical metamaterial having a negative refractive index, and
the photonic lattice structure comprises a slab structure of a photonic crystal.

16. The electron microscopy apparatus according to claim 1, wherein the detector device is arranged for collecting
an energy loss spectrum of the sample,
a cathodoluminescence signal of the sample,
a diffraction pattern of the sample, or
a bright-field or dark-field image of the sample.

17. A sample supply device being arranged for providing a sample in an electron microscopy apparatus according to claim 11, comprising
the sample holder for arranging the sample in the electron probe path of the electron microscopy apparatus,
the photonic lattice structure, and
a support structure carrying the sample holder and the photonic lattice structure.

18. The sample supply device according to claim 17, further comprising
a manipulating and actuating unit being arranged for adjusting a distance between the sample holder and the photonic lattice structure.

* * * * *